US009155864B2

(12) United States Patent
Stout et al.

(10) Patent No.: US 9,155,864 B2
(45) Date of Patent: Oct. 13, 2015

(54) MULTIPLE USE BLOOD CONTROL VALVE WITH CENTER AND CIRCUMFERENTIAL SLITS

(71) Applicants: Marty L. Stout, South Jordan, UT (US); Austin Jason McKinnon, Herriman, UT (US)

(72) Inventors: Marty L. Stout, South Jordan, UT (US); Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 337 days.

(21) Appl. No.: 13/644,841

(22) Filed: Oct. 4, 2012

(65) Prior Publication Data

US 2013/0090610 A1    Apr. 11, 2013

Related U.S. Application Data

(60) Provisional application No. 61/544,158, filed on Oct. 6, 2011.

(51) Int. Cl.
*A61M 25/14* (2006.01)
*A61M 25/00* (2006.01)
(Continued)

(52) U.S. Cl.
CPC ....... *A61M 25/0097* (2013.01); *A61M 25/0606* (2013.01); *A61M 39/045* (2013.01); *A61M 39/0693* (2013.01); *A61M 2039/064* (2013.01); (Continued)

(58) Field of Classification Search
CPC ................... A61M 39/045; A61M 2039/0036; A61M 2039/0081; A61M 2039/027; A61M 2039/064; A61M 2039/066; A61M 2039/0653; A61M 2039/0673; A61M 39/0693; A61M 2039/1072

USPC .............. 604/256, 34, 99.04, 167.02, 167.04, 604/201; 251/149.1, 335.2
See application file for complete search history.

(56) References Cited

U.S. PATENT DOCUMENTS 4,387,879 A    6/1983   Tauschinski
4,449,693 A    5/1984   Gereg
(Continued)

FOREIGN PATENT DOCUMENTS

CA          2 133 053           3/1995
DE    20 2009 009 602 U1    12/2009
(Continued)

OTHER PUBLICATIONS

Elson Silva, PhD, "Respecting Hydrology Science in the Patenting System," pp. 1-7, Jan. 13, 2011.

*Primary Examiner* — Nicholas Lucchesi
*Assistant Examiner* — Justin L Zamory
(74) *Attorney, Agent, or Firm* — Jeanne Lukasavage; Craig Metcalf; Kirton McConkie (57) ABSTRACT

A system for controlling fluid flow in a catheter assembly is disclosed. The system comprises an intravenous catheter assembly with a catheter adapter. The catheter adapter comprises an inner lumen with a septum disposed within a portion of the inner lumen. The septum has a barrier capable of being deformed from a relaxed position to a biased position. The barrier further comprises a slit having a closed configuration and an opened configuration. The slit is in the closed configuration when the barrier is in the relaxed position and in the opened configuration when the barrier is in the biased position. The barrier is configured to be mechanically deformed from the relaxed position to the biased position by a septum actuator that advances against a proximal surface of the barrier without traversing the barrier.

19 Claims, 10 Drawing Sheets

(51) Int. Cl.
*A61M 39/04* (2006.01)
*A61M 39/06* (2006.01)
*A61M 25/06* (2006.01)

(52) U.S. Cl.
CPC .. *A61M 2039/066* (2013.01); *A61M 2039/0653* (2013.01)

(56) References Cited

U.S. PATENT DOCUMENTS

| | | |
|---|---|---|
| 4,616,768 A | 10/1986 | Flier |
| 4,758,225 A | 7/1988 | Cox et al. |
| 4,842,591 A | 6/1989 | Luther |
| 4,874,377 A | 10/1989 | Newgard et al. |
| 4,917,668 A | 4/1990 | Haindl |
| 4,935,010 A | 6/1990 | Cox et al. |
| 4,950,257 A | 8/1990 | Hibbs et al. |
| 5,041,097 A | 8/1991 | Johnson |
| 5,053,014 A | 10/1991 | Van Heugten |
| 5,062,836 A | 11/1991 | Wendell |
| 5,064,416 A | 11/1991 | Newgard et al. |
| 5,084,023 A | 1/1992 | Lemieux |
| 5,085,645 A | 2/1992 | Purdy et al. |
| 5,108,374 A | 4/1992 | Lemieux |
| 5,127,905 A | 7/1992 | Lemieux |
| 5,154,703 A | 10/1992 | Bonaldo |
| 5,156,596 A | 10/1992 | Balbierz et al. |
| 5,234,410 A | 8/1993 | Graham et al. |
| 5,290,246 A | 3/1994 | Yamamoto et al. |
| 5,295,969 A | 3/1994 | Fischell et al. |
| 5,330,435 A | 7/1994 | Vaillancourt |
| 5,350,363 A | 9/1994 | Goode et al. |
| 5,352,205 A | 10/1994 | Dales et al. |
| 5,405,323 A | 4/1995 | Rogers et al. |
| 5,456,675 A | 10/1995 | Wolbring et al. |
| 5,487,728 A | 1/1996 | Vaillancourt |
| 5,520,666 A | 5/1996 | Choudhury et al. |
| 5,549,566 A | 8/1996 | Elias et al. |
| 5,549,577 A | 8/1996 | Siegel et al. |
| 5,575,769 A | 11/1996 | Vaillancourt |
| 5,613,663 A | 3/1997 | Schmidt et al. |
| 5,651,772 A | 7/1997 | Arnett |
| 5,657,963 A | 8/1997 | Hinchliffe et al. |
| 5,697,915 A | 12/1997 | Lynn |
| 5,738,144 A | 4/1998 | Rogers |
| 5,743,884 A * | 4/1998 | Hasson et al. ............ 604/167.02 |
| 5,749,861 A | 5/1998 | Guala et al. |
| 5,806,831 A | 9/1998 | Paradis |
| 5,817,069 A | 10/1998 | Arnett |
| 5,911,710 A | 6/1999 | Barry et al. |
| 5,954,698 A | 9/1999 | Pike |
| 5,967,490 A | 10/1999 | Pike |
| 6,039,302 A | 3/2000 | Cote, Sr. et al. |
| 6,077,244 A | 6/2000 | Botich et al. |
| 6,117,108 A | 9/2000 | Woehr et al. |
| 6,171,287 B1 | 1/2001 | Lynn et al. |
| 6,273,869 B1 | 8/2001 | Vaillancourt |
| 6,485,473 B1 | 11/2002 | Lynn |
| 6,575,960 B2 | 6/2003 | Becker et al. |
| 6,595,981 B2 | 7/2003 | Huet |
| 6,699,221 B2 | 3/2004 | Vaillancourt |
| 6,719,726 B2 | 4/2004 | Meng et al. |
| 6,740,063 B2 | 5/2004 | Lynn |
| 6,883,778 B1 | 4/2005 | Newton et al. |
| 7,008,404 B2 * | 3/2006 | Nakajima ................ 604/158 |
| 7,347,839 B2 | 3/2008 | Hiejima |
| 7,396,346 B2 | 7/2008 | Nakajima |
| 7,470,254 B2 | 12/2008 | Basta et al. |
| 7,736,339 B2 | 6/2010 | Woehr et al. |
| 7,914,494 B2 | 3/2011 | Hiejima |
| 2006/0163515 A1 | 7/2006 | Ruschke |
| 2007/0083157 A1 | 4/2007 | Belley et al. |
| 2007/0083162 A1 | 4/2007 | O'Reagan et al. |
| 2007/0233007 A1 | 10/2007 | Adams |
| 2008/0039796 A1 | 2/2008 | Nakajima |
| 2008/0108944 A1 | 5/2008 | Woehr et al. |
| 2009/0259175 A1 | 10/2009 | Nordgren |
| 2010/0204648 A1 * | 8/2010 | Stout et al. ................ 604/122 |
| 2010/0204675 A1 | 8/2010 | Woehr et al. |
| 2010/0222746 A1 | 9/2010 | Burkholz |
| 2011/0046570 A1 | 2/2011 | Stout et al. |

FOREIGN PATENT DOCUMENTS

| | | |
|---|---|---|
| EP | 1 679 043 A1 | 7/2006 |
| WO | 93/11696 | 6/1993 |
| WO | 98/00195 | 1/1998 |
| WO | 99/34849 | 7/1999 |
| WO | 2006/059540 A1 | 6/2006 |
| WO | 2008/052790 A2 | 5/2008 |
| WO | 2009/114833 A1 | 9/2009 |
| WO | 2010/093791 A1 | 8/2010 |

* cited by examiner

MULTIPLE USE BLOOD CONTROL VALVE WITH CENTER AND CIRCUMFERENTIAL SLITS

RELATED APPLICATIONS

This application claims priority to U.S. Provisional Patent Application No. 61/544,158, entitled "MULTIPLE USE BLOOD CONTROL VALVE WITH CENTER AND CIRCUMFERENTIAL SLITS," filed Oct. 6, 2011, which is incorporated herein in its entirety.

BACKGROUND OF THE INVENTION

The current invention relates to infusion devices, specifically to peripheral intravenous (IV) catheters. In particular, the invention relates to a flushable peripheral IV catheter assembly having features to enable selective activation of fluid flow through the catheter assembly.

Catheters are commonly used for a variety of infusion therapies. For example, catheters are used for infusing fluids, such as normal saline solution, various medicaments, and total parenteral nutrition, into a patient, withdrawing blood from a patient, or monitoring various parameters of the patient's vascular system.

Catheters and/or needles are typically coupled to a catheter adapter to enable attachment of IV tubing to the catheter. Thus, following placement of the catheter or needle into the vasculature of a patient, the catheter adapter is coupled to a fluid source via a section of IV tubing. In order to verify proper placement of the needle and/or catheter in the blood vessel, the clinician generally confirms that there is "flashback" of blood in a flashback chamber of the catheter assembly.

Once proper placement of the catheter is confirmed, the clinician must then attach the catheter adapter to a section of IV tubing, or continue to manually occlude the vein to prevent undesirable exposure to blood. The process of coupling the catheter adapter to the section of IV tubing requires the clinician to awkwardly maintain pressure on the vein of the patient while simultaneously coupling the catheter adapter and the IV tubing. A common, yet undesirable practice is to permit blood to temporarily and freely flow from the catheter adapter while the clinician locates and couples the IV tubing to the catheter adapter. Another common practice is to attach the catheter adapter to the IV tubing prior to placing the needle or catheter into the vein of the patient. While this method may prevent undesirable exposure to blood, positive pressure within the IV line may also prevent desirable flashback.

Some catheter assemblies further utilize a septum actuator and a split septum, wherein the septum actuator is mechanically advanced through a slit of the septum to provide a fluid pathway through the septum. However, once advanced through the septum, the septum actuator becomes lodged within the slit of the septum and is unable to return to its initial position. As such, the fluid pathway remains in an opened position thereby enabling uncontrolled flow of fluids through the septum.

Accordingly, there is a need in the art for a catheter assembly that permits user controlled fluid flow, yet provides desirable flashback without the risk of encountering undesirable exposure to blood. Such a catheter assembly is disclosed herein.

BRIEF SUMMARY OF THE INVENTION

In order to overcome the limitations discussed above, the present invention relates to a flushable peripheral IV catheter assembly having features to enable selective activation of fluid flow through the catheter assembly. The catheter assembly of the present invention generally includes a catheter coupled to a catheter adapter. The catheter generally includes a metallic material, such as titanium, surgical steel or an alloy as is commonly known in the art. In some embodiments, a polymeric catheter may be used in combination with a metallic introducer needle, as is commonly known and used in the art.

In some embodiments of the present invention, a septum is positioned within a lumen of the catheter assembly to prevent or limit flow of a fluid through the catheter adapter. The septum generally includes a flexible or semi-flexible material that is compatible with exposure to blood, medicaments, and other fluids commonly encountered during infusion procedures. In some embodiments, a groove is provided on an inner surface of the catheter adapter, wherein the septum is seated within the groove. As such, the position of the septum within the catheter adapter is maintained.

In some implementations of the present invention, a closed or partially closed pathway, such as a slit or plurality of slits is further provided in a barrier surface of the septum. The pathway permits fluid to bypass the septum and flow though the catheter adapter. In some embodiments, the pathway is a slit that is closed prior to being opened or activated by a probe or septum actuator positioned within the lumen of the catheter adapter. Prior to being opened or activated, the slit prevents passage of fluid through the catheter adapter. Thus, in some embodiments a plurality of air vent channels are interposed between the septum and the groove to permit air flow through the catheter adapter prior to the slit being opened. The air vents prevent buildup of positive pressure within the catheter adapter thereby permitting flashback of blood into the catheter and a forward chamber of the catheter adapter.

The septum actuator generally includes a plastic or metallic tubular body having a probing end and a contact end. The probing end is positioned adjacent to the pathway of the septum, and the contact end is positioned adjacent to a proximal opening of the catheter adapter. The probing end of the septum actuator is advanced against the septum when a probe is inserted into the proximal opening of the catheter adapter. As the probe contacts the contact surface of the septum actuator, the septum actuator is advanced in a distal direction thereby deforming the barrier surface of the septum and a distal direction. When in the biased position, the slits in the barrier surface assume an opened position thereby enabling free flow of fluid through the catheter assembly.

Finally, the presence of the septum actuator within the lumen of the catheter adapter may result in aberrant fluid flow leading to undesirable stagnation and coagulation of fluids within the catheter assembly. Thus, in some embodiments of the present invention the septum actuator further includes various features such as flow deflectors and/or flow diversion channels, to maintain proper fluid flow within the catheter adapter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
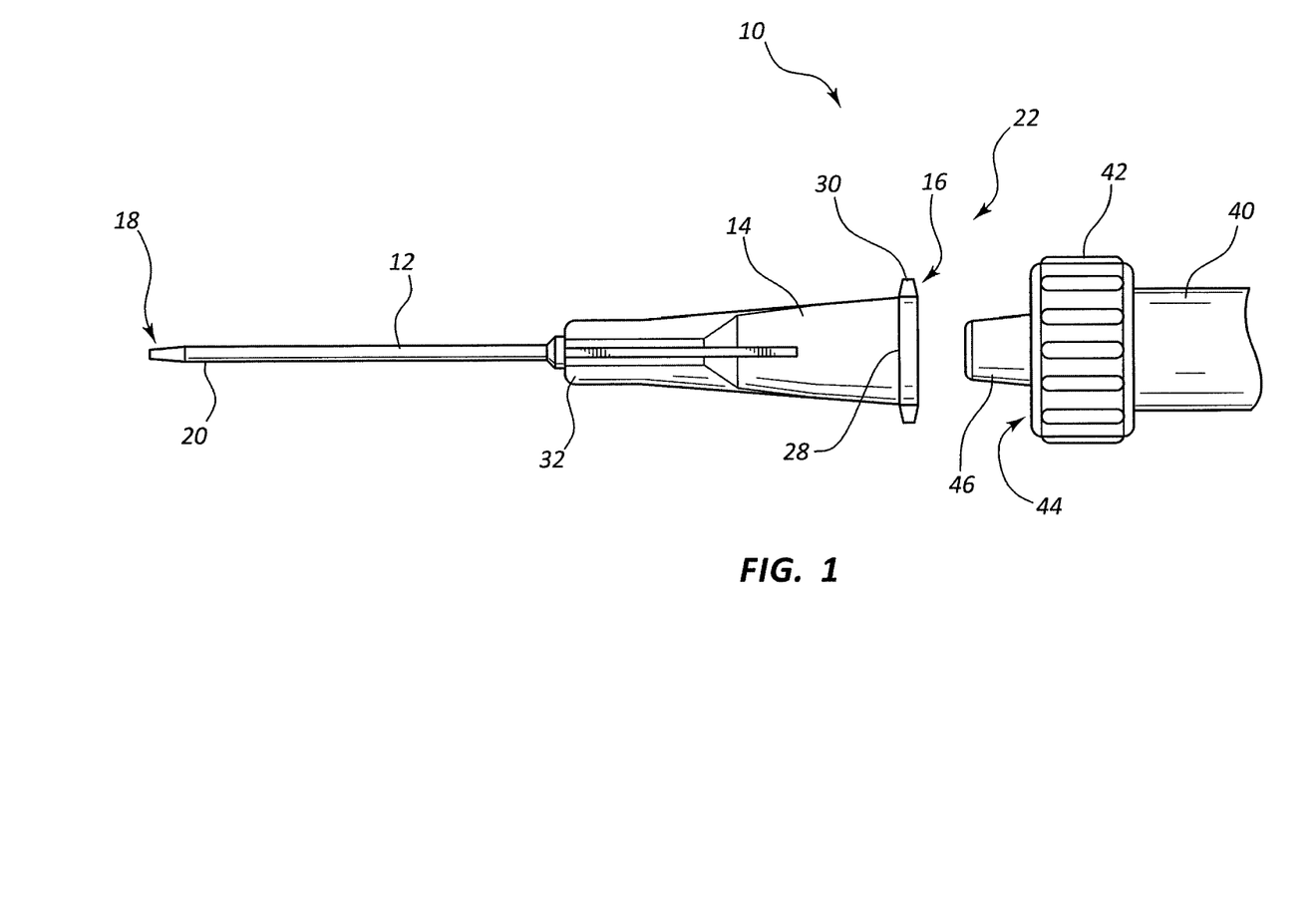
FIG. 1 is a perspective view of an embodiment of a catheter assembly in accordance with a representative embodiment of the present invention.

Referring now to FIG. 1, a catheter assembly 10 is illustrated. The catheter assembly 10 generally includes a catheter 12 coupled to a distal end 32 of a catheter adapter 14. The catheter 12 and the catheter adapter 14 are integrally coupled such that an internal lumen 16 of the catheter adapter 14 is in fluid communication with a lumen 18 of the catheter 12. The catheter 12 generally comprises a biocompatible material having sufficient rigidity to withstand pressures associated with insertion of the catheter into a patient. In some embodiments, the catheter 12 comprises a flexible or semi-flexible polymer material, such as silicone, polyurethane, or polytetrafluoroethylene. Catheter 12 may further comprises a rigid metallic material, such as titanium, stainless steel, nickel, molybdenum, surgical steel, and alloys thereof. In some instances, catheter 12 comprises a flexible polymer material that is used in combination with a rigid cannula, such as an introducer needle (not shown) to assist in the catheterization process.

One of skill in the art will appreciate that the features of the present invention may be incorporated for use with an over-the-needle catheter assembly. For example, one of skill in the art will appreciate that a flexible or semi-flexible polymer catheter may be used in combination with a rigid introducer needle to enable insertion of the catheter into a patient. One of skill in the art will further appreciate that surgically implanted catheters may also be used in combination with the present invention.

Once inserted into a patient, the catheter 12 and catheter adapter 14 provide a fluid conduit to facilitate delivery of a fluid to and/or retrieval of a fluid from a patient, as required by a desired infusion procedure. Thus, in some embodiments the material of the catheter 12 and the catheter adapter 14 are selected to be compatible with bio-fluids and medicaments commonly used in infusion procedures. Additionally, in some embodiments a portion of the catheter 12 and/or catheter adapter 14 is configured for use in conjunction with a section of intravenous tubing 40 to further facilitate delivery of a fluid to or removal of a fluid from a patient.

In some embodiments, a proximal end 22 of the catheter adapter 14 includes a flange 28. The flange 28 provides a positive surface which may be configured to enable coupling of an intravenous tubing or patient conduit 40 to the catheter assembly 10. In some embodiments, the flange 28 includes a set of threads 30. The threads 30 are generally provided and configured to compatibly receive a complementary set of threads 44 comprising a portion of a male Luer or conduit coupler 42. The conduit coupler 42 is generally coupled to an end portion of the patient conduit 40 in a fluid-tight manner. In some embodiments, an inner portion of the conduit coupler 42 is extended outwardly to provide a probe surface 46.

The probe surface 46 is generally configured to compatibly insert within a proximal end 22 of the catheter adapter 14. Following insertion of the probe 46 into the proximal end 22 of the catheter adapter 14, the conduit coupler 42 is rotated to interlock the coupler 42 and the flange 28 (via the sets of threads 30 and 44). During the process of interlocking the coupler 42 and the flange 28, the probe surface 46 is advanced into the lumen 16 of the catheter adapter 14 to an inserted position. The inserted position of the probe surface 46 activates the catheter assembly 10 to enable flow of fluid through the catheter 12 and catheter adapter 14. Once the conduit coupler 42 and the catheter adapter 14 are attached, a fluid may be delivered to a patient via the patient conduit 40 and the inserted catheter 12.

Figure 2:
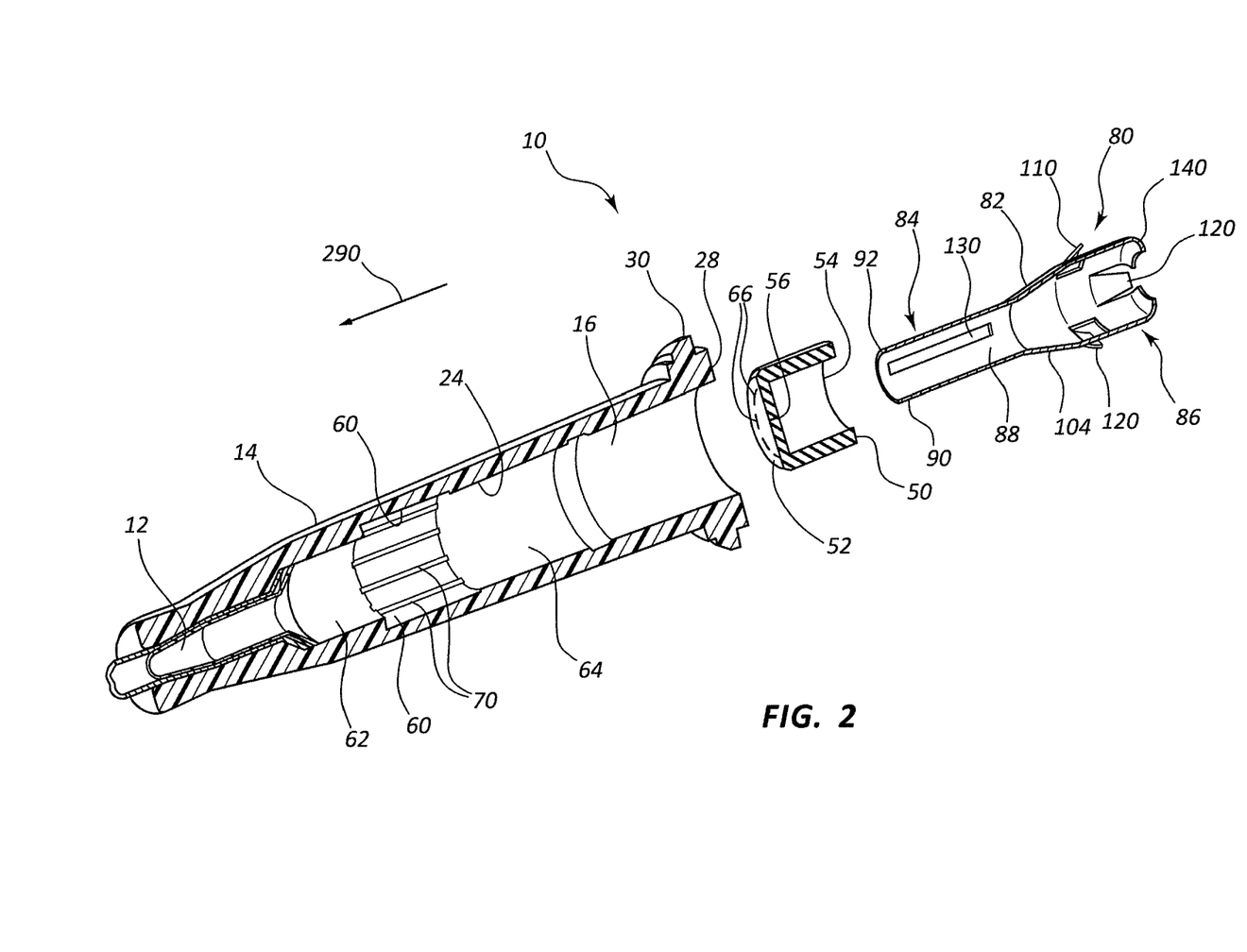
FIG. 2 is an exploded cross-sectioned view of a catheter assembly in accordance with a representative embodiment of the present invention.

Referring now to FIG. 2, an exploded, cross-sectional view of a catheter assembly 10 is shown. In some embodiments, the catheter adapter 14 includes various design features and components to control and/or limit flow of fluid through the catheter assembly 10. For example, in some embodiments of the present invention a septum 50 is positioned within the inner lumen 16 of the catheter adapter 14. The septum 50 generally comprises a flexible, or semi-flexible elastomeric polymer plug, such as silicone or TPE. Septum 50 generally comprises an outer diameter that is configured to compatibly seat within a groove or channel 60 formed on an inner surface 24 of the catheter adapter 14. In some embodiments, the septum 50 is barrel or can shaped having a barrier surface 52 comprising a distal end of the septum 50 and further having an opening 54 comprising a proximal end of the septum 50. When positioned within the channel 60, barrier surface 52 of the septum 50 divides the inner lumen 16 of the catheter adapter 14 into a forward fluid chamber 62 and a rearward fluid chamber 64. The presence of septum 50 controls or limits passage of fluid between the forward and rearward fluid chambers 62 and 64. Specifically, a chosen configuration of the barrier surface 52 of the septum 50 largely determines the ability of a fluid to flow through the inner lumen 16 of the catheter adapter 14.

For example, in some embodiments the barrier surface 52 of the septum 50 is configured to include a slit 56. The slit 56 is configured to provide selective access or flow of a fluid through the barrier surface 52. In some embodiments, the slit 56 is configured to remain in a closed, fluid-tight position until activated or biased into an opened configuration by advancing a septum actuator 80 against barrier surface 52 in a distal direction 290. In some embodiments, the barrier surface 52 comprises one slit 56. In other embodiments, the barrier surface 52 is modified to include multiple slits 56 and 66, as shown. In particular, in some embodiments barrier surface 52 comprises a center slit 56 and a plurality of circumferential slits 66. Center slit 56 may include any configuration, and in some embodiments comprises a tri-slit configuration. Circumferential slits 66 may also include any configuration, and in some embodiments comprise a plurality of arched slits.

In general, center slit 56 and circumferential slits 66 form a fluid tight seal prior to being actuated by septum actuator 80. However, for some infusion therapy techniques, it may be desirable to permit a controlled flow of fluid through the septum 50 prior to activating the septum 50 with the septum actuator 80. Thus, in some embodiments center slit 56 does not form a fluid tight seal. Rather, center slit 56 forms a leak orifice to permit controlled flow of liquid or air between the forward and rearward chambers 62 and 64.

The groove or channel 60 into which the septum is seated comprises a recessed portion of the inner surface 24 of the catheter adapter 14. The outer diameter of the septum 50 is generally configured to compatibly and securely seat within the channel 60. For example, in some embodiments the outer diameter of the septum 50 is selected to be both slightly smaller than the diameter of the channel 60 and slightly larger than the diameter of the inner lumen 16. As such, the septum 50 is retained within the channel 60 during use of the catheter assembly 10.

For some infusion therapy techniques, air flow between the forward and rearward chambers 62 and 64 may be desirable. For example, for those embodiments comprising a septum 50 having a fluid-tight slit 56 and 66, passage of air from the forward chamber 62 to the rearward chamber 64 is prohibited prior to opening or actuating septum 50 via septum actuator 80, as previously discussed. Thus, when the catheter 12 of the catheter assembly 10 is inserted into the vascular system of a patient, a positive pressure develops within the forward chamber 62 thereby preventing a desired flashback of the patient's blood into the catheter adapter 14. An observable flashback is generally desirable to confirm accurate placement of the catheter tip 20 within the vein of the patient. Thus, some embodiments of the present invention include features or elements to enable airflow between the forward chamber 62 and the rearward chamber 64, without requiring activation of the septum 50 with the septum actuator 80. As such, some embodiments of the present invention provide an observable flashback, as generally desired for infusion procedures.

For example, in some embodiments center slit 56 is modified so as to permit controlled leakage of air or liquid, as previously discussed. In other embodiments, a plurality of air vent channels 70 is interposed between the septum 50 and the inner surface 24 of the catheter adapter 14. The air vent channels 70 relieve the positive pressure within the forward chamber 62 by providing an access for air to bypass the septum 50 into the rearward chamber 64. In some embodiments, the air vent channels 70 are constructed by removing portions of the channel 60 surface, resulting in a plurality of generally parallel grooves. In other embodiments, an outer surface of septum 50 is modified to include a plurality of generally parallel grooves (not shown), as shown and taught in U.S. patent application Ser. No. 12/544,625, which is incorporated herein by reference.

With continued reference to FIG. 2, septum actuator 80 comprises a probe-like structure that is primarily housed in the rearward chamber 64 of the catheter adapter 14. Septum actuator 80 generally comprises a tubular body 82 having a distal end 84 and a proximal end 86. The tubular body 82 comprises a rigid or semi-rigid material, such as a plastic or metallic material. The tubular body 82 further comprises an inner lumen 88 for facilitating flow of a fluid and/or liquid through the septum actuator 80. Septum actuator 80 may further include various features 110, 120 and 130 to retain septum actuator 80 within catheter adapter 14, and to optimize fluid flow through and around septum actuator 80.

The distal end 84 of the tubular body 82 is configured to compatibly abut and thereby the form barrier surface 52 of septum 50. Distal end 84 is generally configured to compatibly insert within opening 54 of septum 50. The distal end 84 further includes a probing surface 90 which extends through the opening 54 of the septum 50 to a position proximal to the barrier surface 52 of the septum 50. The probing surface 90 is advanced against barrier surface 52 as septum actuator 80 is advanced through the catheter adapter 14 in distal direction 290. In some embodiments, probing surface 90 comprising a minimum outer diameter that is selected to be greater than the maximum opening size 57 of center slit 56 when septum 50 is actuated. As such, probing surface 90 is prevented from passing through center slit 56. The inability of probing surface 90 to pass through center slit 56 causes septum actuator 80 to return to its starting position following the removal of conduit coupler 42 from catheter adapter 14, wherein septum 50 resumes its initial, relaxed configuration. In some instances, the diameter of probing surface 90 is constant over the entire length of septum actuator 80.

Figure 3A:
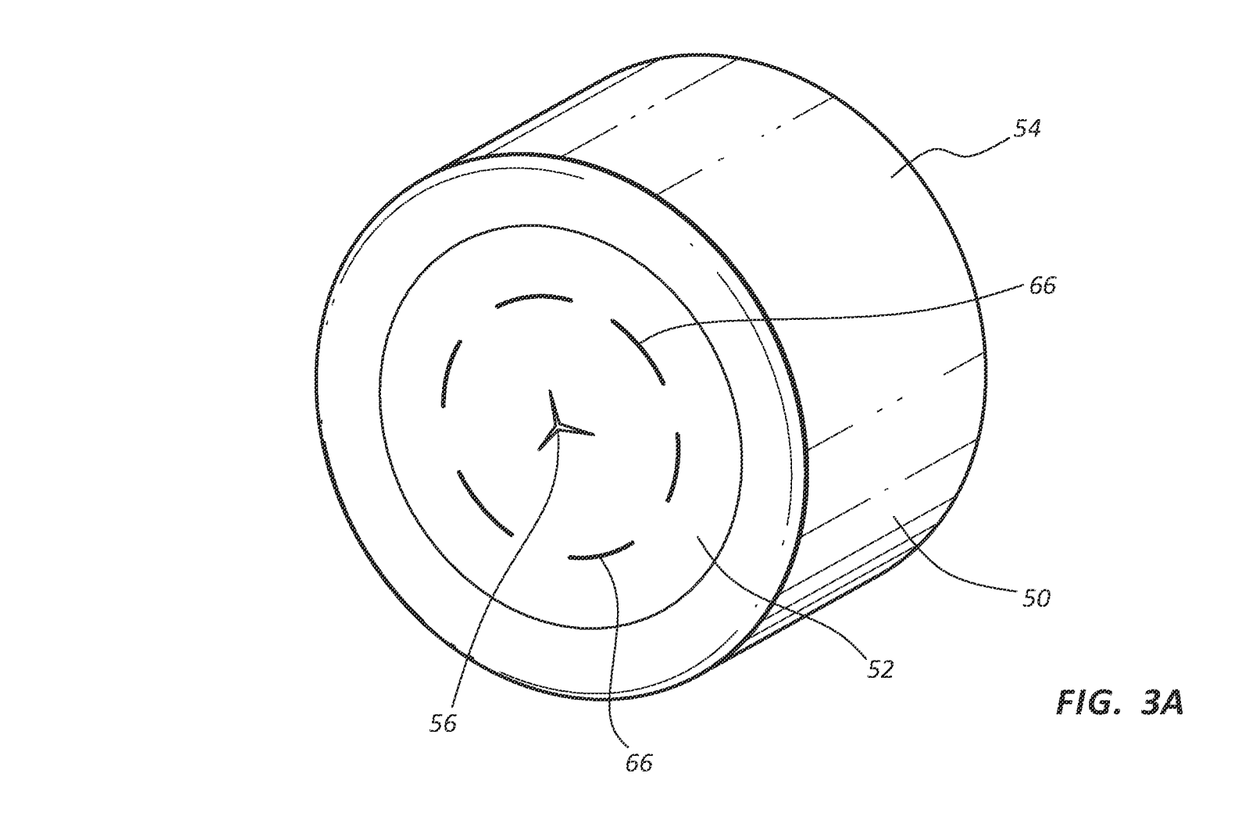
FIG. 3A is a perspective view of an un-actuated septum in accordance with a representative embodiment of the present invention.
Figure 3B:
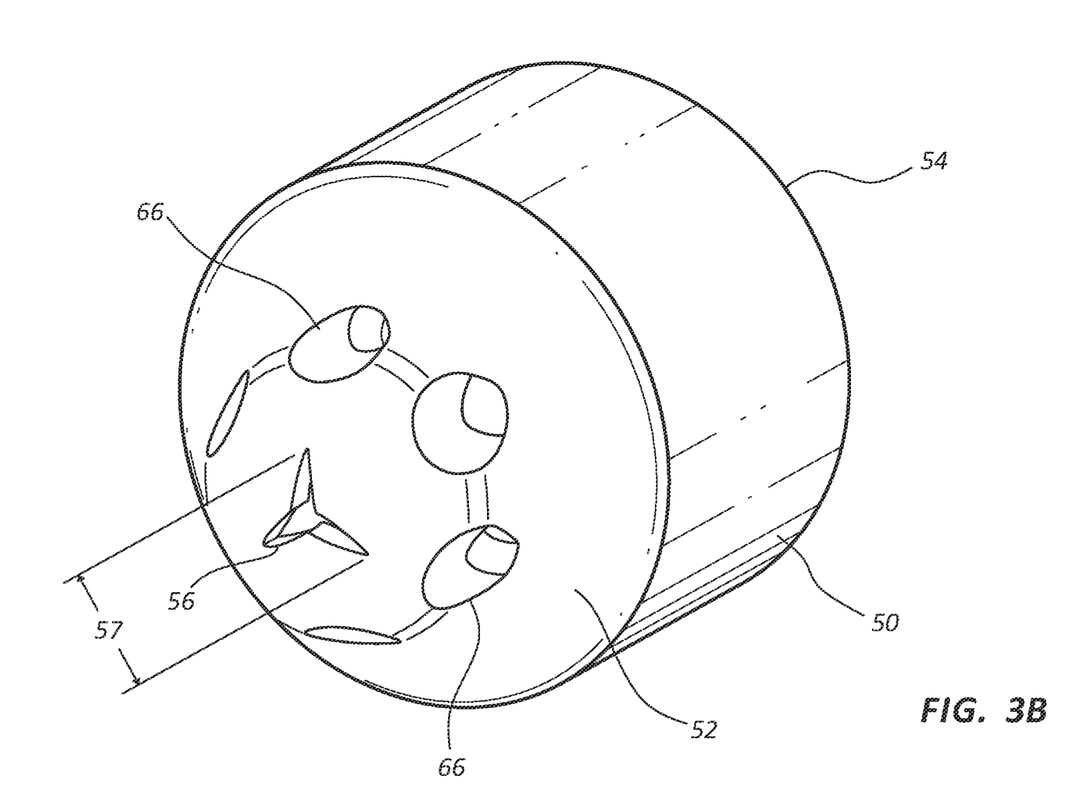
FIG. 3B is a perspective view of an actuated septum in accordance with a representative embodiment of the present invention.

Referring now to FIGS. 3A and 3B, septum 50 is shown. The shapes and configuration of center slit 56 and circumferential slits 66 are generally provided so as to have a relaxed, closed configuration prior to actuation, as shown in FIG. 3A, and a deformed, opened configuration subsequent to actuation, as shown in FIG. 3B. Accordingly, barrier surface 52 of septum 50 generally comprises elastic properties whereby barrier surface 52 is permitted to be elastically deformed, and thereafter return to its initial, relaxed configuration. When deformed, slits 56 and 66 are biased into an open position thereby permitting fluid and air to bypass barrier surface 52 and flow freely between forward and rearward fluid chambers 62 and 64.

Figure 3C:
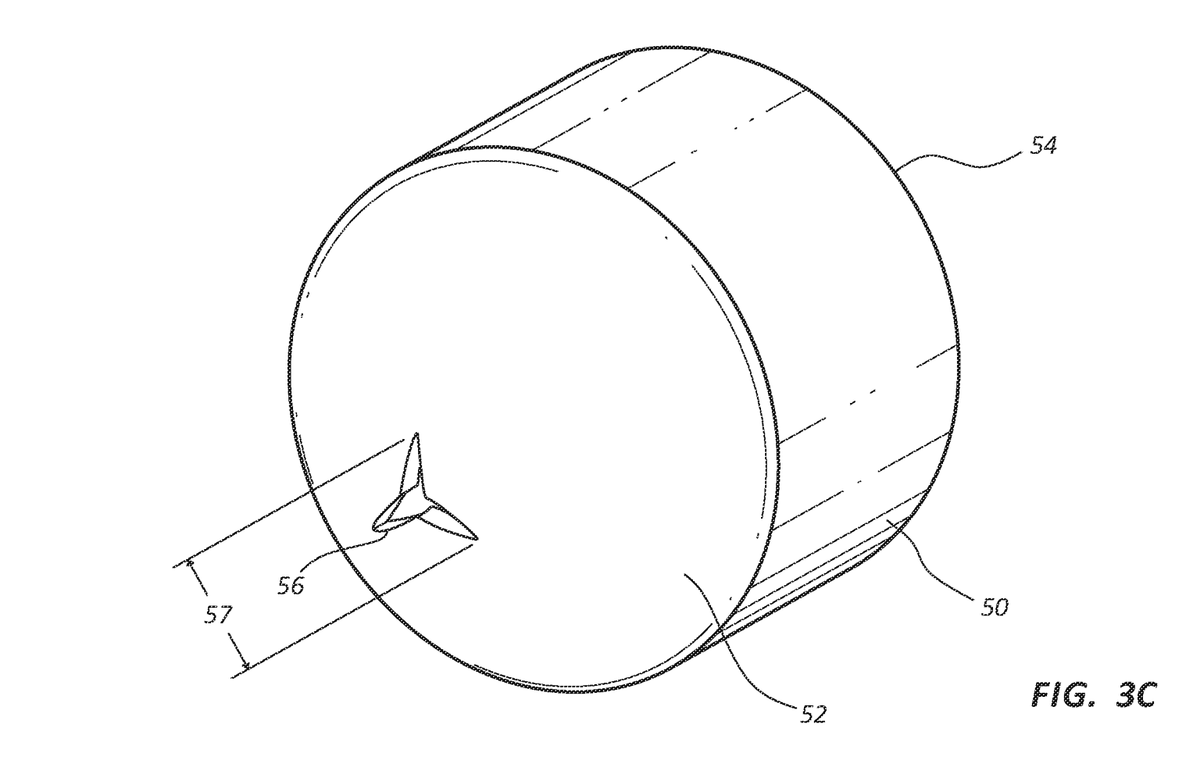
FIG. 3C is a perspective view of an actuated septum having a center slit in accordance with a representative embodiment of the present invention.

Septum 50 may include any configuration of slits in accordance with the teaching of the present invention. For example, in some embodiments septum 50 comprises a single, center slit 56, as shown in FIG. 3C. Center slit 56 comprises a maximum opening size 57 that is configured to be smaller than the minimum outer diameter of probing surface 90 of septum actuator 80. As such, septum actuator 80 is prevented from passing through center slit 56 as septum actuator 80 is advanced in distal direction 290.

Figure 3D:
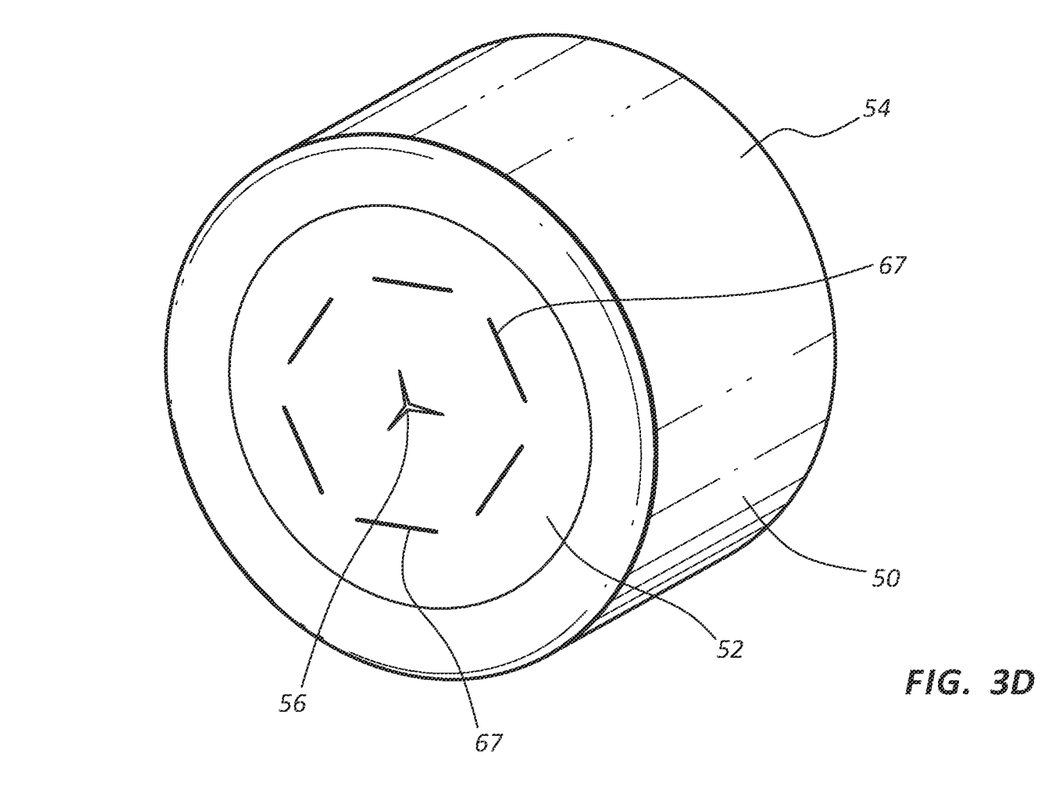
FIG. 3D is a perspective view of an un-actuated septum having a plurality is straight slits in a circumferential pattern in accordance with a representative embodiment of the present invention.
Figure 3E:
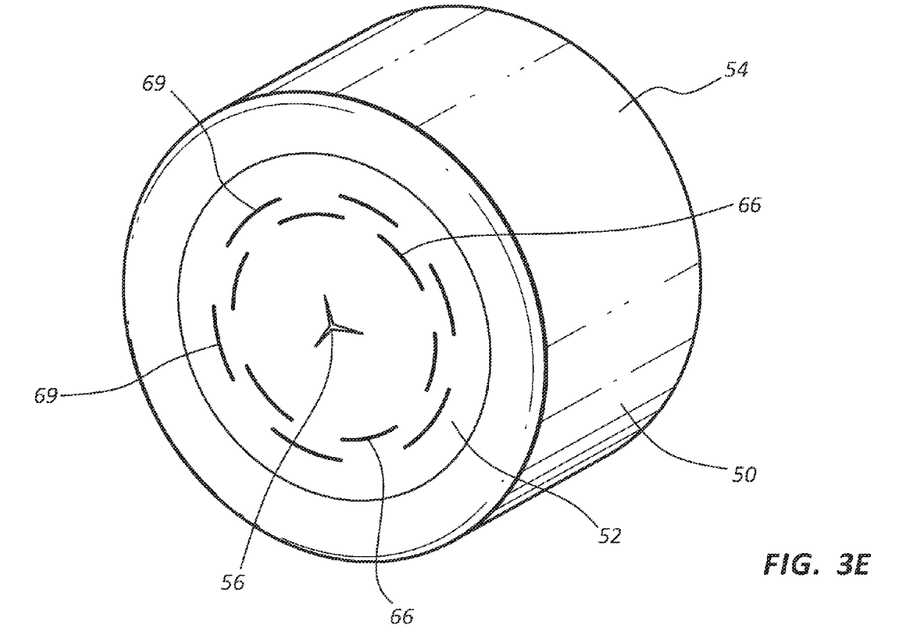
FIG. 3E is a perspective view of an un-actuated septum having two sets of staggered circumferential slits in accordance with a representative embodiment of the present invention.

In other embodiments, septum 50 comprises a plurality of straight, circumferential slits 67, as shown in FIG. 3D. Generally, circumferential slits 67 are positioned radially about center slit 56 such that a length of each slit 67 is approximately perpendicular to a radial line extending outwardly from the center of septum 50. In other embodiments, septum 50 comprises two or more sets of circumferential slits, as shown in FIG. 3E. Septum 50 may comprise a first set of circumferential slits 66 provided at a first radial distance from center slit 56, and further comprise a second set of circumferential slits 69 provided at a second radial distance from center slit 56, wherein the second distance is greater than the first distance. Further, in some embodiments the first and second sets of circumferential slits 66 and 69 are staggered and/or partially overlapping.

Those of ordinary skill in the art will appreciate that the specific configurations and orientations of center and circumferential slits of the present invention may be practiced in any variety of ways to accomplish the teachings of the instant invention. Accordingly, the various embodiments shown in the Figures of the present invention are not intended to be limiting. Rather, the Figures are provided merely as a means for demonstrating the underlying principles of the present invention.

Figure 4A:
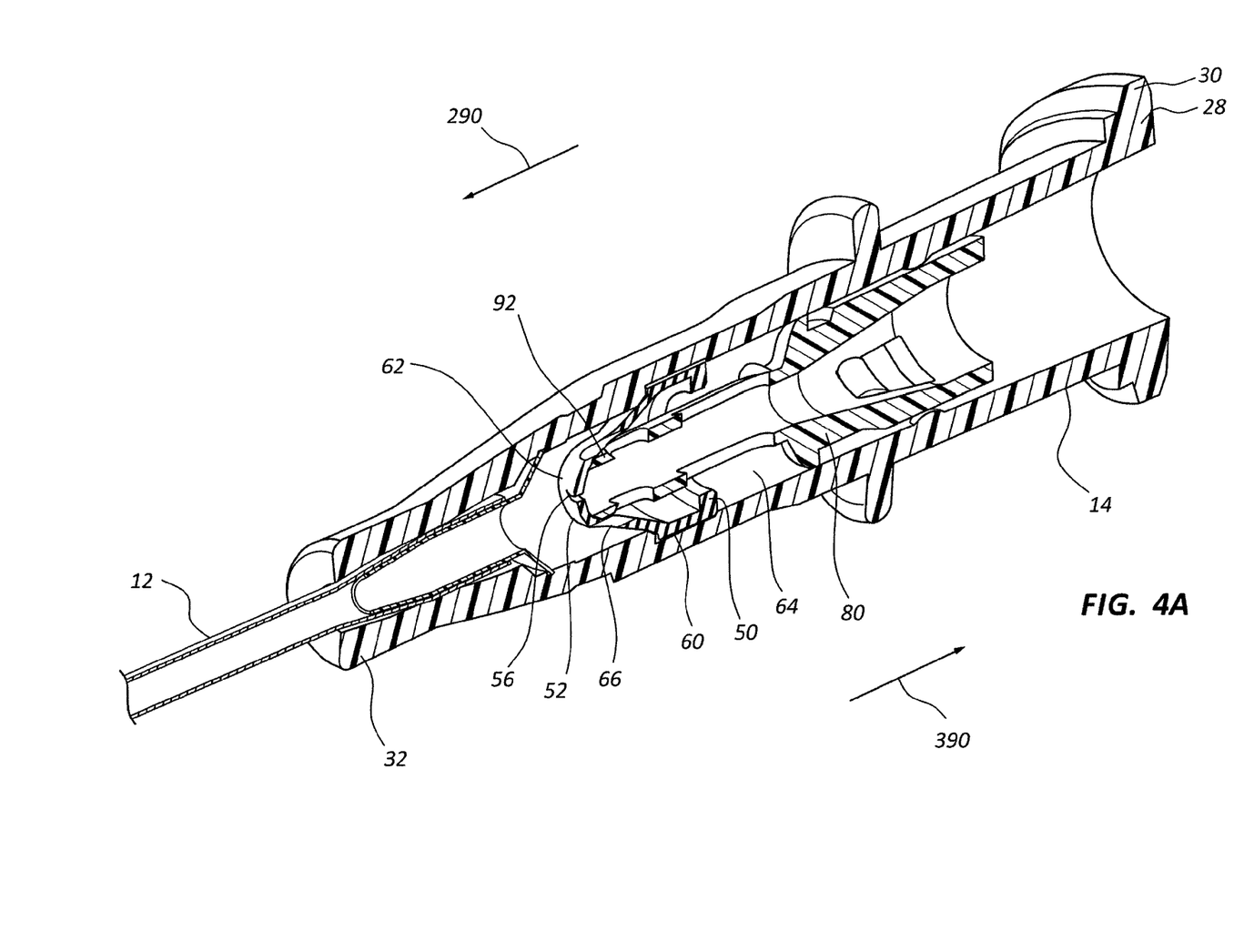
FIG. 4A is a cross-sectioned view of an assembled catheter assembly in accordance with a representative embodiment of the present invention, following activation.
Figure 4B:
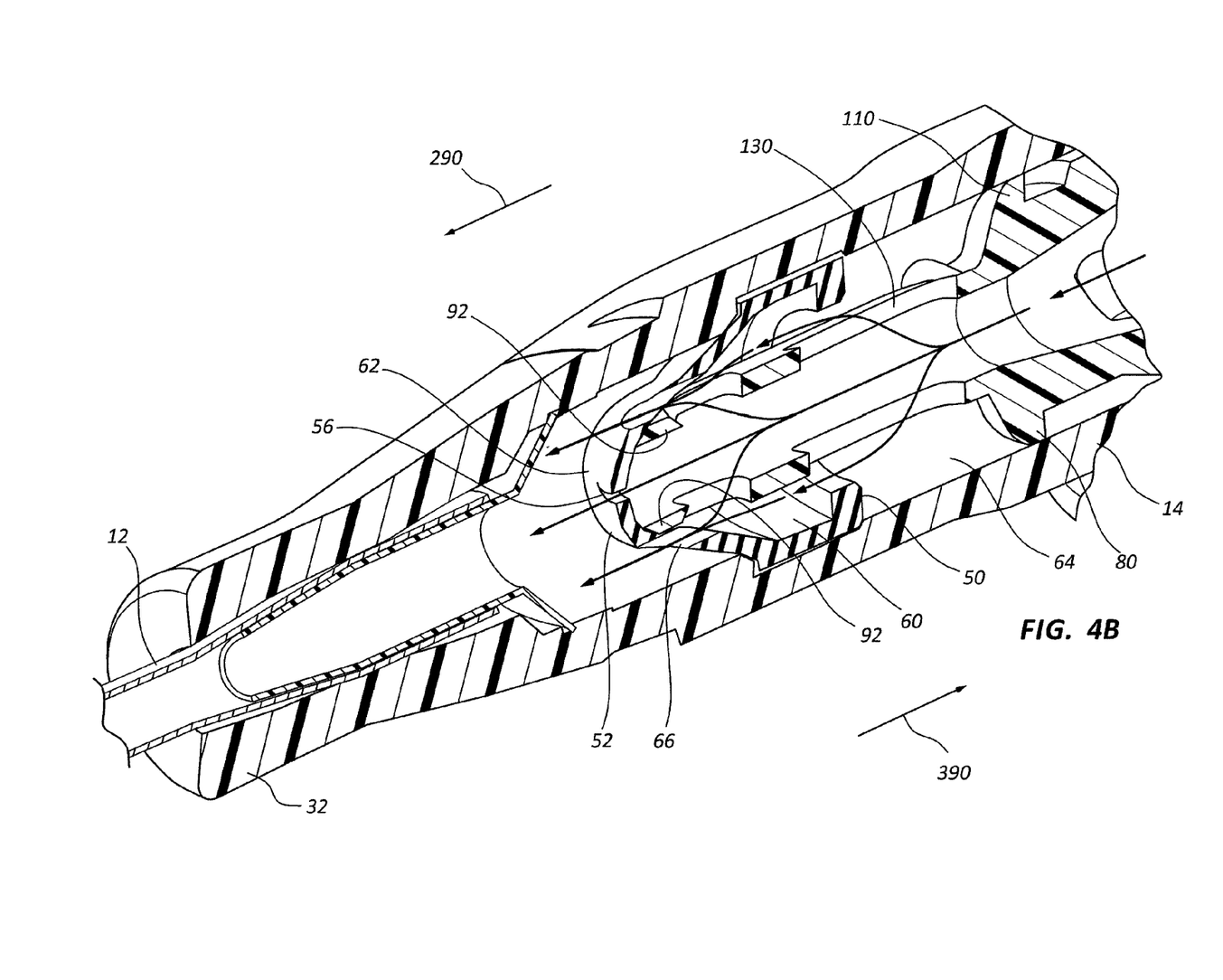
FIG. 4B is a detailed, cross-sectioned view of an assembled catheter assembly in accordance with a representative embodiment of the present invention, following activation.
Figure 5:
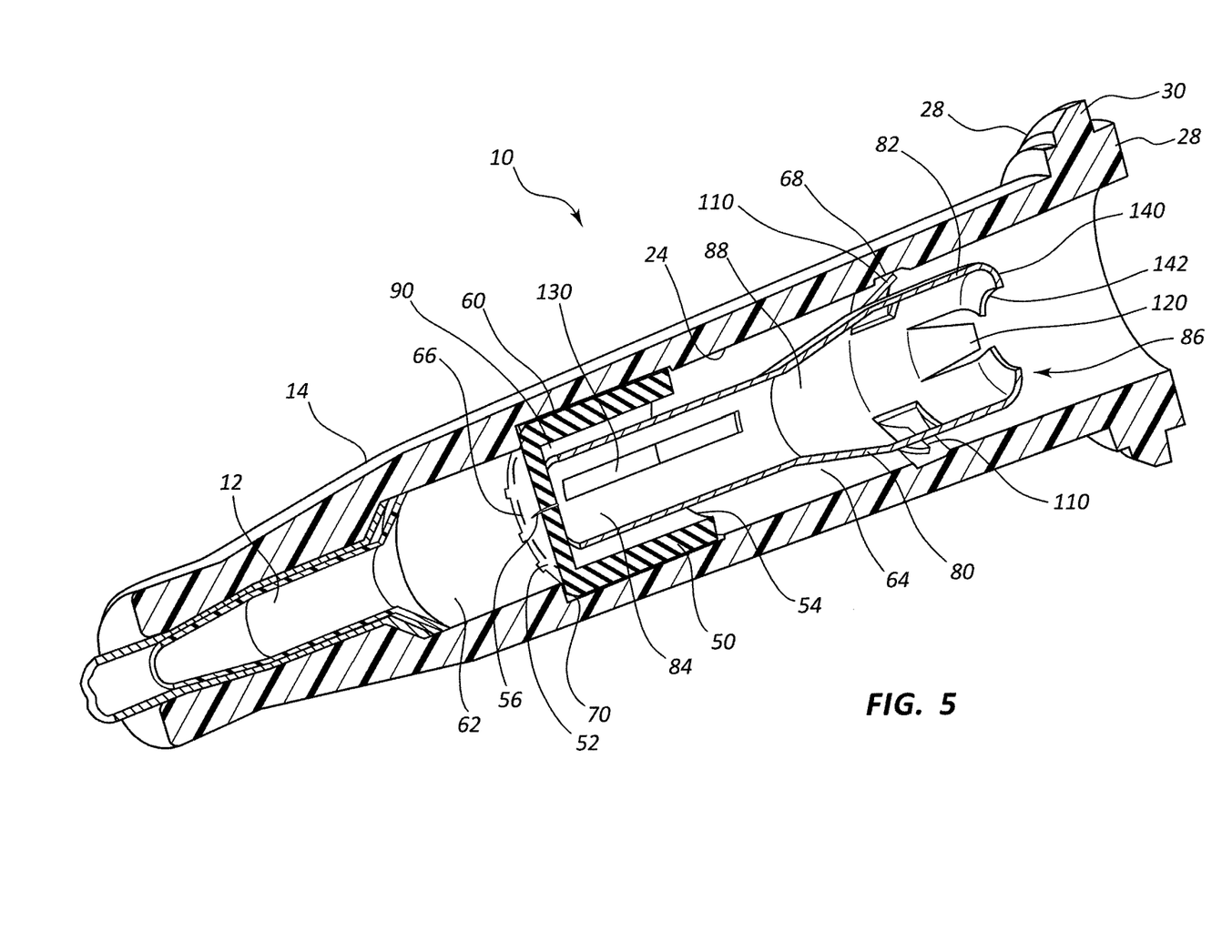
FIG. 5 is a cross-sectioned view of an assembled catheter assembly in accordance with a representative embodiment of the present invention, prior to activation.

Referring now to FIG. 4A, septum 50 and barrier surface 52 are shown in a deformed, actuated configuration. In some embodiments, septum actuator 80 is advanced within catheter adapter 14 in a distal direction 290 such that leading-edge 92 of septum actuator 80 contacts and biases the inner surface of barrier surface 52 thereby deforming barrier surface 52, center slit 56 and circumferential slits 66 in a distal direction 290. As such, center slit 56 and circumferential slit 66 are opened thereby permitting free flow of fluids between forward fluid chamber 62 and rearward fluid chamber 64, a shown in FIG. 5B. Upon releasing septum activator 80, the elastic or resilient properties of barrier surface 52 reposition septum activator 80 in a proximal direction 390 thereby enabling barrier surface 52, center slit 56 and circumferential slits 66 to resume their initial, relaxed configuration, as shown in FIG. 5. Accordingly, the fluid tight configuration of septum 50 is reestablished.

In some embodiments, catheter assembly 10 further comprises and introducer needle (not shown) to assist a user in accessing the patient's vein during the catheterization process. Center slit 56 permits passage of the introducer needle through septum 50, thereby enabling a sharpened tip of the introducer needle to extend distally beyond the tip portion 20 of the catheter 12. Following the catheterization procedure, the introducer needle is removed from the catheter assembly 10 and is safely disposed.

In some embodiments, the introducer needle is coated with a significant amount of silicone or similar fluid, such as fluorosilicone. The purpose of the coating fluid is threefold. Firstly, the coating fluid acts as a lubricant between the outer surface of the introducer needle and the interfacing surfaces of center slit 56. Thus, upon withdrawal of the introducer needle from the septum 50, the coating fluid prevents undesirable adhesion between the outer surface of the introducer needle and the interfacing surfaces of center slit 56. Secondly, excess coating fluid accumulates within center slit 56 thereby assisting in sealing septum 50 to prevent blood from flowing back through the septum following removal of the introducer needle. Excess coating fluid accumulates within center slit 56 as introducer needle is removed from catheter assembly 10. In particular, when the introducer needle is being withdrawn through septum 50, the interfacing surfaces of center slit 56 act to wipe the coating fluid from the outer surface of the introducer needle thereby displacing the coating fluid into center slit 56. Thirdly, the coating fluid acts as a lubricant to prevent undesirable adhesion between opposing surfaces of center slit 56.

The coating fluid may include any biocompatible lubricant. In some embodiments, the coating fluid comprises a lubricant such as a non-wetting lubricant that is applied to an interface between the introducer needle and the center slit 56 to further eliminate possible leakage of fluid and/or air. A non-wetting lubricant may also be beneficial to prevent tearing or other damage to the slit that may occur when the needle is removed from the catheter assembly following catheterization. A non-wetting lubricant may also facilitate proper realignment of the opposing surfaces of center slit 56 following removal of the introducer needle. Non-limiting examples of a non-wetting lubricant include known Teflon based non-wetting materials such as Endura, from Endura Coating Co.; A20, E-20, 1000-S20, FEP Green, PTFE and X-40 from Tiodize; Cammie 2000 from AE Yale; 21845 from Ladd Research; MS 122-22, MS 122DF, MS-143DF, MS-122V MS-122VM, MS143V, MS-136W, MS-145W, U0316A2, U0316B2, MS-123, MS-125, MS-322 and MS-324 from Miller-Stepheson; and 633T2 from Otto Bock can also be used. Various non-Teflon based non-wetting lubricant type materials include Dylyn, from ART; Nyebar, Diamonex, NiLAD, TIDLN, Kiss-Cote, Titanium oxide; Fluocad Fluorochemical Coating FC-722, from 3M; Permacote from Dupont; Plasma Tech 1633 from Plasma Tech, Inc.; and silicone sprays and dips from Nusil and/or Dow Chemical.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A septum, comprising a body having a proximal end and a distal end, the proximal end having an opening and the distal end forming a barrier, the barrier being capable of being deformed from a relaxed position to a biased position, the barrier further comprising a slit having a closed configuration and an opened configuration, wherein the slit comprises the closed configuration when the barrier is in the relaxed position, and the slit comprises the opened configuration when the barrier is in the biased position;

wherein the barrier is configured to be mechanically deformed from the relaxed position to the biased position by a septum actuator that advances against a proximal surface of the barrier, the slit having a maximum opening size that is less than an outer diameter of a distal end of the septum actuator such that the distal end of the septum actuator is prevented from traversing the barrier when the barrier is in the biased position.

2. The septum of claim 1, wherein the closed configuration is fluid tight.

3. The septum of claim 1, wherein the septum comprises an elastic material.

4. The septum of claim 1, wherein the septum is resilient.

5. The septum of claim 1, wherein the slit comprises a plurality of slits.

6. The septum of claim 5, wherein the plurality of slits comprises a center slit surrounded by a plurality of elongated slits, each of the elongated slits being arranged circumferentially around the center slit.

7. The septum of claim 6, wherein the plurality of elongated slits comprises at least one of a plurality of arched slits and a plurality of straight slits.

8. The septum of claim 1, wherein the slit is a center slit.

9. A system for controlling fluid flow in a catheter assembly, comprising:

an intravenous catheter assembly having a catheter adapter comprising an inner lumen;

a septum disposed within a portion of the inner lumen, the septum having a barrier capable of being deformed from a relaxed position to a biased position, the barrier further comprising a slit having a closed configuration and an opened configuration, wherein the slit comprises the closed configuration when the barrier is in the relaxed position, and the slit comprises the opened configuration when the barrier is in the biased position;

wherein the barrier is configured to be mechanically deformed from the relaxed position to the biased position by a septum actuator that advances against a proximal surface of the barrier, the slit having a maximum opening size that is less than an outer diameter of a distal end of the septum actuator such that the distal end of the septum actuator is prevented from traversing the barrier when the barrier is in the biased position.

10. The system of claim 9, wherein the septum actuator is disposed within a portion of the inner lumen adjacent to the septum, the distal end of the septum actuator contacting a proximal surface of the septum, and a proximal end of the septum actuator being positioned adjacent to an opening of the catheter adapter, wherein the proximal end of the septum actuator is accessed by inserting an external device into the opening of the catheter adapter.

11. The system of claim 10, further comprising a lumen forming a fluid pathway through the septum actuator.

12. The system of claim 9, further comprising a ventilation channel interposed between the septum and an inner surface of the inner lumen of the catheter adapter, the ventilation channel having a surface area and a perimeter selected to permit passage of at least one of air and blood at a desired rate of flow.

13. The system of claim 10, wherein the proximal surface of the septum further includes a cavity for housing the distal end of the septum actuator.

14. The system of claim 9, wherein the slit comprises a center slit surrounded by a plurality of elongated arched slits arranged circumferentially around the center slit.

15. The system of claim 10, wherein the septum actuator is slidably housed within the portion of the inner lumen and is capable of moving between a proximal position and a distal position, wherein when the septum actuator is in the proximal position the septum is in the relaxed position, and wherein when the septum actuator is in the distal position, the distal end of the septum actuator biases the septum into the biased position.

16. An intravenous catheter assembly comprising:

a catheter adapter comprising an inner lumen;

a septum disposed within a portion of the inner lumen, the septum comprising a barrier surface for dividing the inner lumen into a distal portion and a proximal portion, the barrier surface including a center slit that extends through a center of the barrier surface, the barrier surface further including a plurality of elongated slits that are arranged circumferentially around the center slit, the center slit being configured to have a maximum opening size defining a diameter of an opening formed by the center slit when the barrier surface is biased in a distal direction; and a septum actuator positioned within the proximal portion of the inner lumen, the septum actuator having a distal end, an outer diameter of the distal end being greater than the maximum opening size of the center slit thereby preventing the distal end of the septum actuator from passing through the center slit when the septum actuator biases the barrier surface in the distal direction.

17. The intravenous catheter assembly of claim 16, wherein the elongated slits are arched slits.

18. The intravenous catheter assembly of claim 16, wherein the elongated slits are straight slits.

19. The intravenous catheter assembly of claim 16, wherein the elongated slits comprise a first set of elongated slits that are circumferentially arranged at a first radial distance from the center of the barrier surface and a second set of elongated slits that are circumferentially arranged at a second radial distance from the center of the barrier surface.

* * * * *